(12) United States Patent
Chang et al.

(10) Patent No.: US 11,911,031 B1
(45) Date of Patent: Feb. 27, 2024

(54) SURGICAL TOOL FOR IMPLANT

(71) Applicant: INDUSTRIAL TECHNOLOGY RESEARCH INSTITUTE, Hsinchu (TW)

(72) Inventors: Fang-Chieh Chang, Keelung (TW); Pei-I Tsai, Hsinchu (TW); Shu-Fen Yeh, New Taipei (TW); Kuo-Yi Yang, Hsinchu (TW); Chih-Chieh Huang, Zhunan Township (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 0 days.

(21) Appl. No.: 18/089,288

(22) Filed: Dec. 27, 2022

(51) Int. Cl.
*A61B 17/072* (2006.01)
*A61B 90/00* (2016.01)

(52) U.S. Cl.
CPC ..... *A61B 17/072* (2013.01); *A61B 2090/0811* (2016.02)

(58) Field of Classification Search
CPC .................................................... A61B 17/072
See application file for complete search history.

(56) References Cited

U.S. PATENT DOCUMENTS

| | | | |
|---|---|---|---|
| 8,163,020 B2 | 4/2012 | Le Huec | |
| 10,568,667 B2 | 2/2020 | Biester et al. | |
| 11,045,232 B2 | 6/2021 | Fischer et al. | |
| 11,135,070 B2 | 10/2021 | Ulrich, Jr. et al. | |
| 2005/0004673 A1 | 1/2005 | Kluger | |
| 2008/0306489 A1 | 12/2008 | Altarac et al. | |
| 2010/0100100 A1 | 4/2010 | Refai et al. | |
| 2011/0034962 A1 | 2/2011 | Dunbar, Jr. et al. | |
| 2015/0134062 A1 | 5/2015 | Fabian | |
| 2019/0059956 A1 | 2/2019 | Milz et al. | |

FOREIGN PATENT DOCUMENTS

| | | |
|---|---|---|
| CN | 108697444 A | 10/2018 |
| CN | 110072481 A | 7/2019 |
| CN | 111712218 A | 9/2020 |
| TW | M422953 U | 2/2012 |

(Continued)

OTHER PUBLICATIONS

K. Tomita, et al., "Total en bloc spondylectomy and circumspinal decompression for solitary spinal metastasis," Paraplegia, vol. 32, Issue 1, pp. 36-46 (Jan. 1994).

(Continued)

*Primary Examiner* — Nathaniel C Chukwurah
(74) *Attorney, Agent, or Firm* — Maschoff Brennan

(57) ABSTRACT

This disclosure relates to a surgical tool configured for holding an implant includes an inner rod and a sleeve. The inner rod includes a rod portion and a holding portion. The holding portion is located at one end of the rod portion and has a first accommodation space configured for accommodating at least part of the implant. The sleeve includes a sleeving portion and a retaining portion. The sleeving portion is slidably sleeved on the rod portion of the inner rod. The retaining portion is located at one end of the sleeving portion and selectively presses against the holding portion. The inner rod further includes at least one fin portion protruded from the holding portion and located in the first accommodation space for being inserted into at least one slot of the implant.

11 Claims, 12 Drawing Sheets

(56) References Cited

FOREIGN PATENT DOCUMENTS

| TW | 201511730 A | 4/2015 |
|---|---|---|
| WO | 2007/074295 A1 | 7/2007 |

OTHER PUBLICATIONS

Alan D. Aaron, et al., "The Management of Cancer Metastatic to Bone," JAMA, vol. 272, Issue 15, pp. 1206-1209 (Oct. 19, 1994).
K. Tomita, et al., "Total en bloc spondylectomy for solitary spinal metastases," International Orthopaedics, vol. 18, Issue 5, pp. 291-298 (Oct. 1994).
Keith H. Bridwell, et al., "Anterior Fresh Frozen Structural Allografts in the Thoracic and Lumbar Spine," Spine, vol. 20, Issue 12, pp. 1410-1418 (Jun. 1995).
S. Boriani, et al., "Reconstruction of the Anterior Column of the Thoracic and Lumbar Spine With a Carbon Fiber Stackable Cage System," Orthopedics, vol. 25, Issue 1, pp. 37-42 (Jan. 2002).
Marcel F. Dvorak, et al., "Effectiveness of Titanium Mesh Cylindrical Cages in Anterior Column Reconstruction After Thoracic and Lumbar Vertebral Body Resection," Spine, vol. 28, Issue 9, pp. 902-908 (May 1, 2003).
Kai-Uwe Lewandrowski, et al., "Anterior Spinal Arthrodesis With Structural Cortical Allografts and Instrumentation for Spine Tumor Surgery," Spine, vol. 29, Issue 10, pp. 1150-1159 (May 15, 2004).
Ashwin Viswanathan, et al., "Initial experience with the use of an expandable titanium cage as a vertebral body replacement in patients with tumors of the spinal column: a report of 95 patients," European Spine Journal, vol. 21, Issue 1, pp. 84-92 (Jan. 2012).
R. Andrew Glennie, et al., "A Systematic Review With Consensus Expert Opinion of Best Reconstructive Techniques After Osseous En Bloc Spinal Column Tumor Resection," Spine, vol. 41, Issue 20S, pp. S205-S211 (Oct. 15, 2016).
Marco Girolami, et al., "Biomimetic 3D-printed custom-made prosthesis for anterior column reconstruction in the thoracolumbar spine: a tailored option following en bloc resection for spinal tumors," European Spine Journal, vol. 27, pp. 3073-3083 (Jul. 23, 2018).
Taiwan Office Action issued in corresponding application No. 111150044, dated Sep. 7, 2023.

SURGICAL TOOL FOR IMPLANT

TECHNICAL FIELD

The present disclosure relates to a surgical tool, more particularly to a surgical tool for an implant.

BACKGROUND

Vertebral bone defects may occur due to tumors, degenerative or infectious diseases. The usual treatment is to remove the damaged or tumor-bearing vertebrae (vertebra) and perform reconstructive surgery. During the reconstructive surgery, doctor uses pedicle screws and spine fixation rods to align the spine and remove the damaged vertebra, and then an implant to be placed into the space created by the removal of the damaged vertebra to reconstruct the spine.

In order to cooperate with the movement of the spine during human activities, some vertebral implants are manufactured to have flexibility through material selection, structural design, etc. This also prevents some problems such as stress concentration at the contact point with vertebrae due to excessive pressure, or slip out of place due to excessively relative movement with vertebrae.

However, the conventional surgical tool, used for inserting a flexible vertebral implant into the space created by the removal of the vertebra, may not be able to effectively position the flexible vertebral implant, so that the flexible vertebral implant is easy to be moved or deformed unwantedly during the insertion, thereby increasing the difficulty of the implant mounting. If the implant is mounted out of place or with unwanted deformation, it may result in fusion failure.

SUMMARY

According to one aspect of the present disclosure, a surgical tool configured for holding an implant includes an inner rod and a sleeve. The inner rod includes a rod portion and a holding portion. The holding portion is located at one end of the rod portion and has a first accommodation space configured for accommodating at least part of the implant. The sleeve includes a sleeving portion and a retaining portion. The sleeving portion is slidably sleeved on the rod portion of the inner rod. The retaining portion is located at one end of the sleeving portion and selectively presses against the holding portion. The inner rod further includes at least one fin portion protruded from the holding portion and located in the first accommodation space for being inserted into at least one slot of the implant.

DETAILED DESCRIPTION

Figure 1:
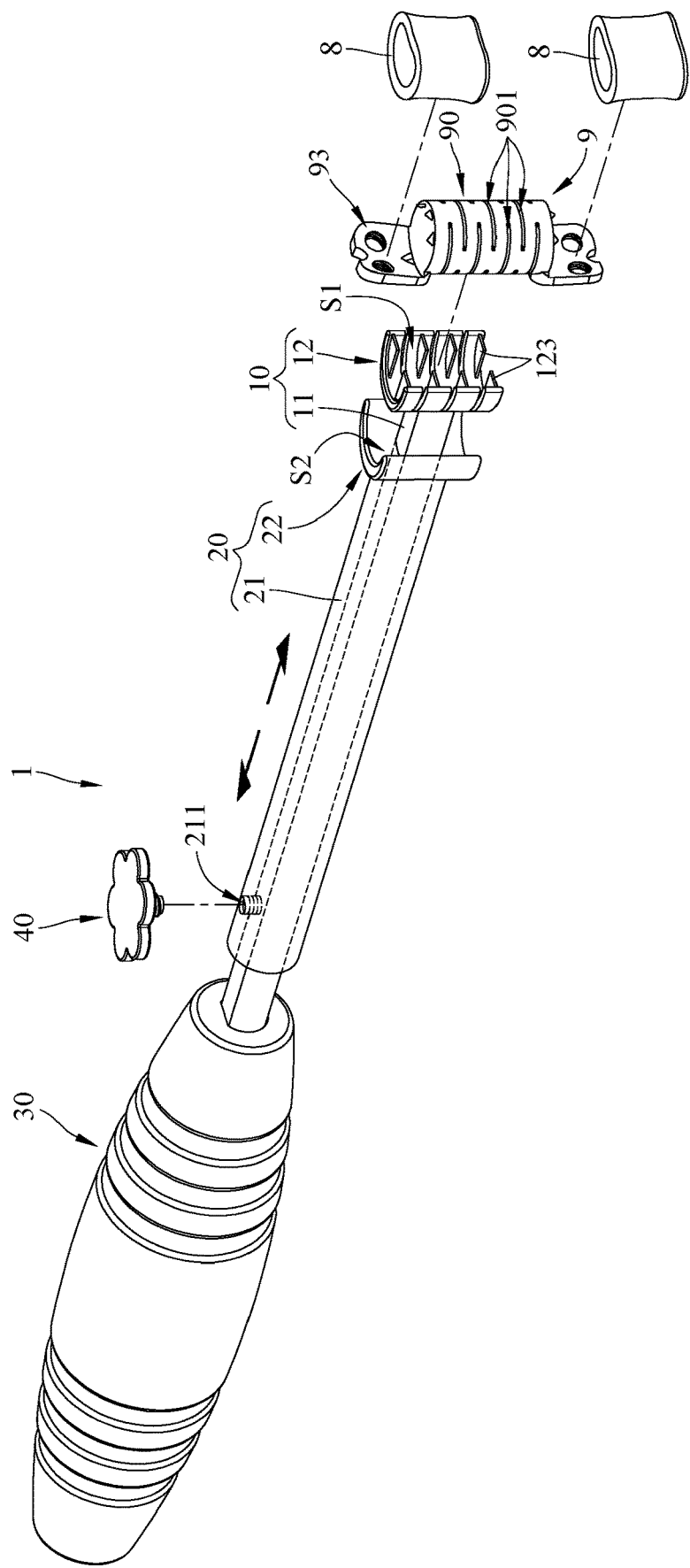
FIG. 1 is a schematic view showing a surgical tool according to one embodiment of the present disclosure being suitable for an implant.

Aspects and advantages of the disclosure will become apparent from the following detailed descriptions with the accompanying drawings. For purposes of explanation, one or more specific embodiments are given to provide a thorough understanding of the disclosure, and which are described in sufficient detail to enable one skilled in the art to practice the described embodiments. It should be understood that the following descriptions are not intended to limit the embodiments to one specific embodiment. On the contrary, it is intended to cover alternatives, modifications, and equivalents as can be included within the spirit and scope of the described embodiments as defined by the appended claims.

As used herein, the terms "substantially" or "approximately" may describe a slight deviation from a target value, so that an effect as present with the target value is maintained. Unless specified or limited otherwise, the phrase "at least one" as used herein may mean that the quantity of the described element or component is one or more than one but does not necessarily mean that the quantity is only one. The term "and/or" may be used herein to indicate that either or both of two stated possibilities. Unless specified or limited otherwise, the terms "mounted", "connected", and variations thereof are used broadly and encompass both direct and indirect mountings and connections.

The present disclosure provides a surgical tool for an implant being capable of effectively positioning the implant during the mounting process of the implant, thereby solving related problems generated by the conventional surgical tool.

The present disclosure provides several exemplary embodiments of the surgical tool for the implant. Generally, please refer to FIG. 1, one exemplary embodiment of the present disclosure provides a surgical tool 1 being beneficial to doctors for mounting an implant 9 into the space between two vertebrae 8. The implant 9 may be, but not limited to, a vertebra reconstruction implant. As shown, the implant 9 is adapted to be implanted into the space created by the removal of one vertebra (i.e., to be implanted between the vertebrae 8) to replace and reconstruct the removed vertebra. Note that the vertebrae 8 exemplarily illustrated as cervical vertebrae herein are not intended to limit the present disclosure.

Specifically, the implant 9 may include a flexible body 90 which refers to the main structure of the implant 9 and is served as a supporter between the vertebrae 8. The flexible body 90 may have one or more slots 901 thereon. The slots 901 may be spaced apart from one another and arranged on the outer surface of the flexible body 90, such that the slots 901 are served as gaps for allowing the flexible body 90 to be bent when being forced. Alternatively, the slots 901 may be helical slots form on the outer surface of the flexible body so that the flexible body 90 becomes a helical structure and therefore has flexible property as a compression spring. Optionally, the implant 9 may further include at least one tab 93 protruded from the flexible body 90. The tab 93 is able to abut on at least one vertebra 8 when the flexible body 90 is mounted between the vertebrae 8, and the tab 93 can be screwed to the at least one vertebrae 8 (e.g., using screws 7 as shown in the following FIG. 10) to firmly secure the mounting of the implant 9. Note that the implant 9 described and depicted herein is only for the purpose of illustration of the surgical tool 1, and the implant 9 itself, the application thereof and the characteristic thereof, such as material, size and shape, configuration or depth of the slots, are not intended to limit the present disclosure.

Figure 2:
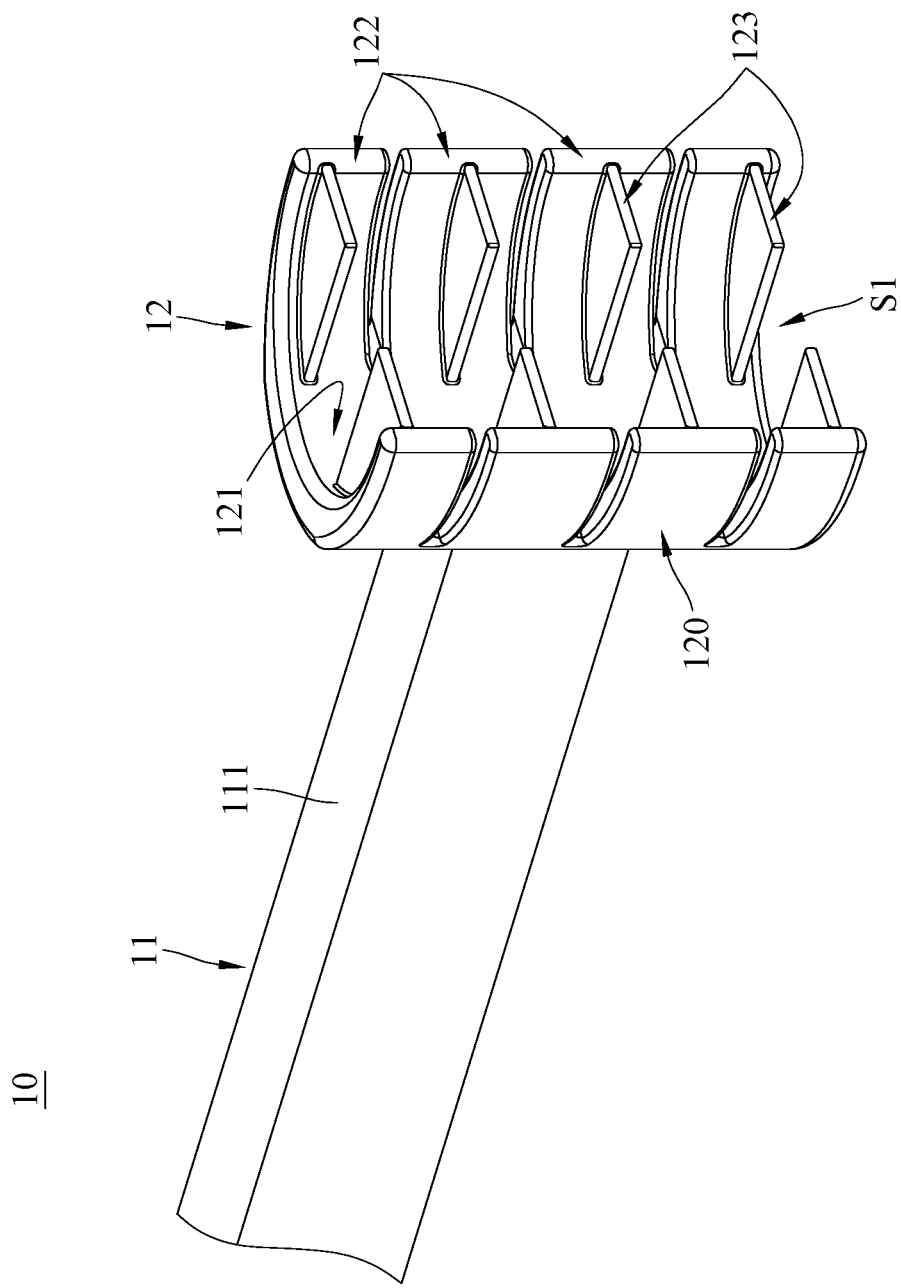
FIG. 2 is a partial and enlarged view of an inner rod of the surgical tool in FIG. 1.
Figure 3:
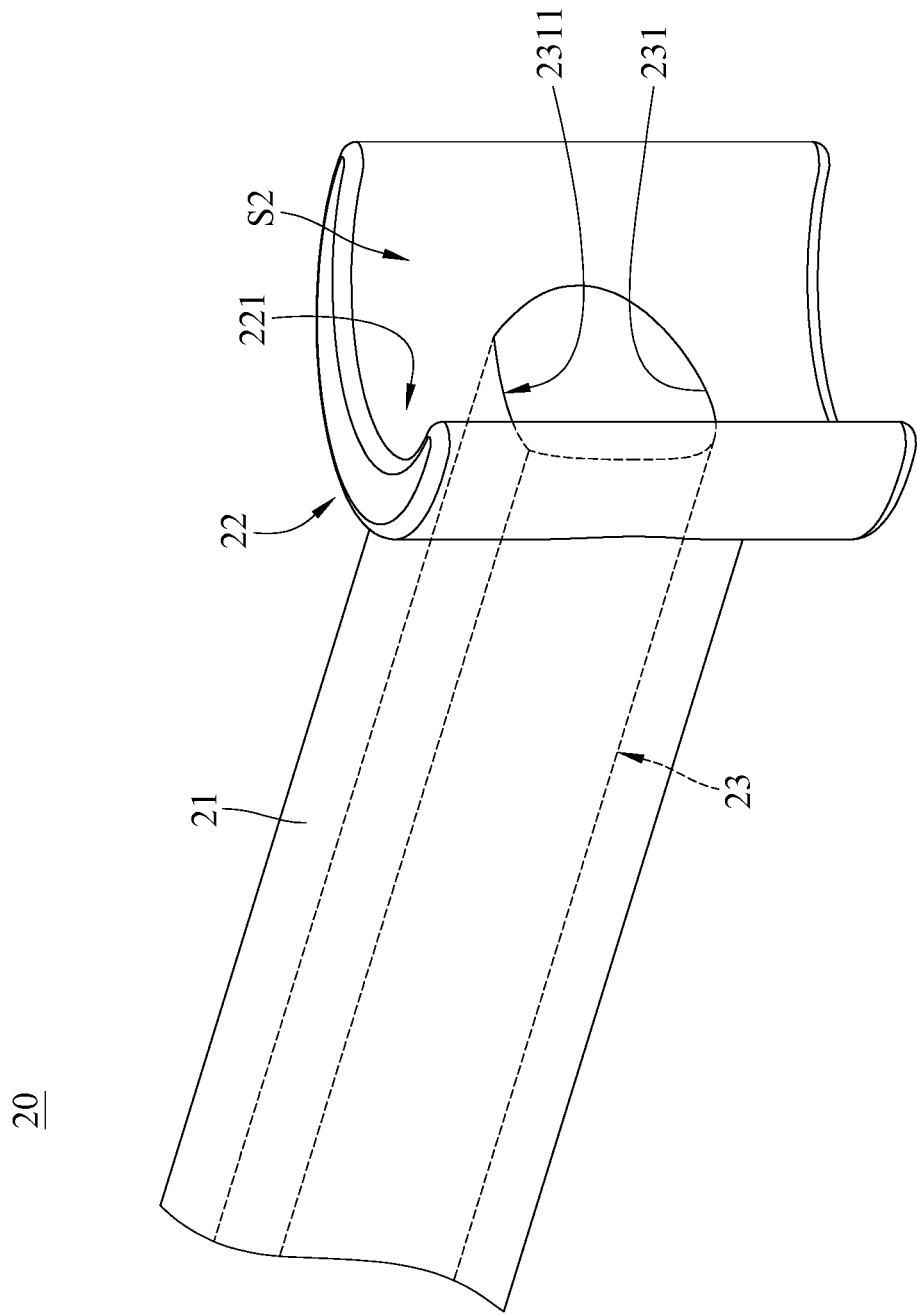
FIG. 3 is a partial and enlarged view of a sleeve of the surgical tool in FIG. 1.
Figure 4:
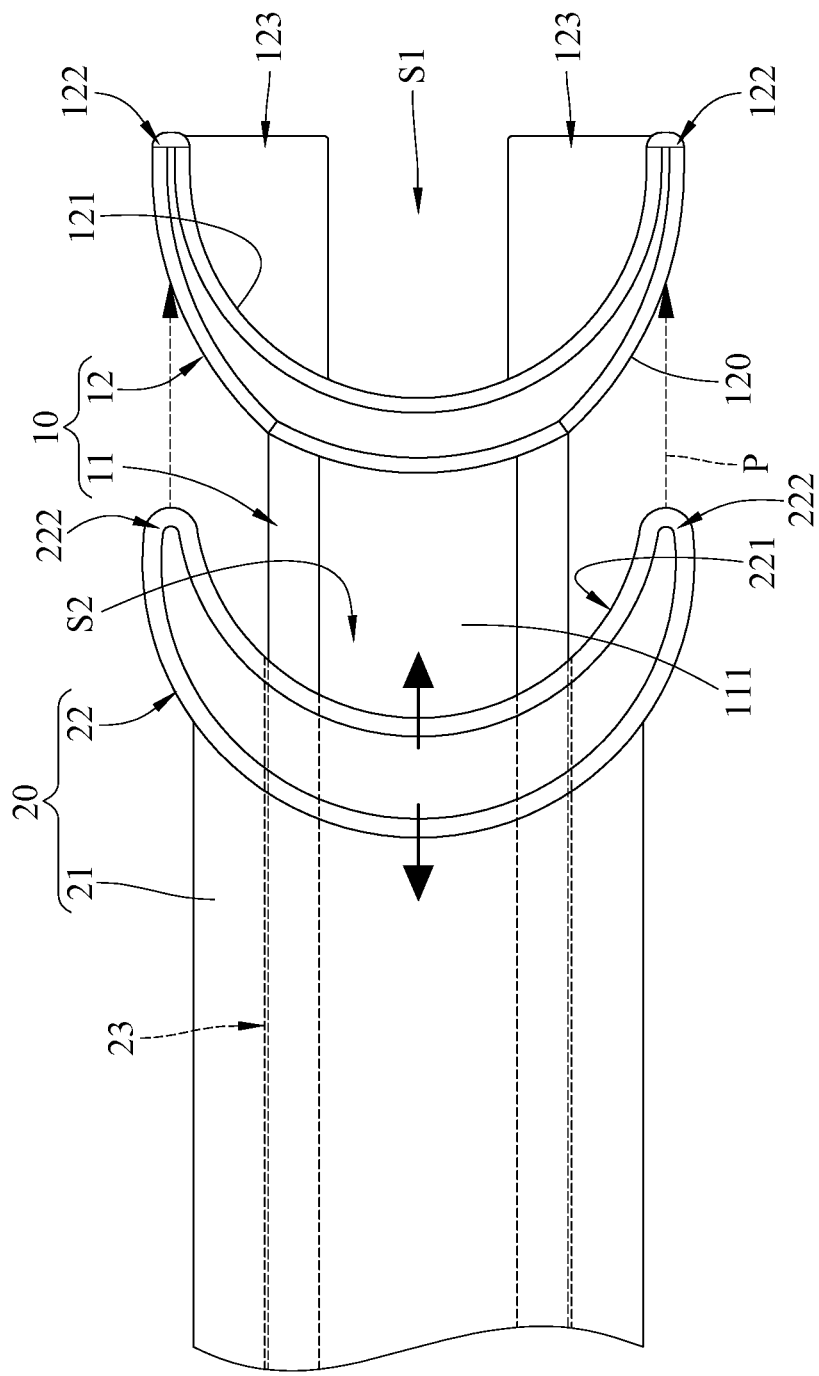
FIG. 4 is a partial and enlarged top view of the surgical tool in FIG. 1.
Figure 5:
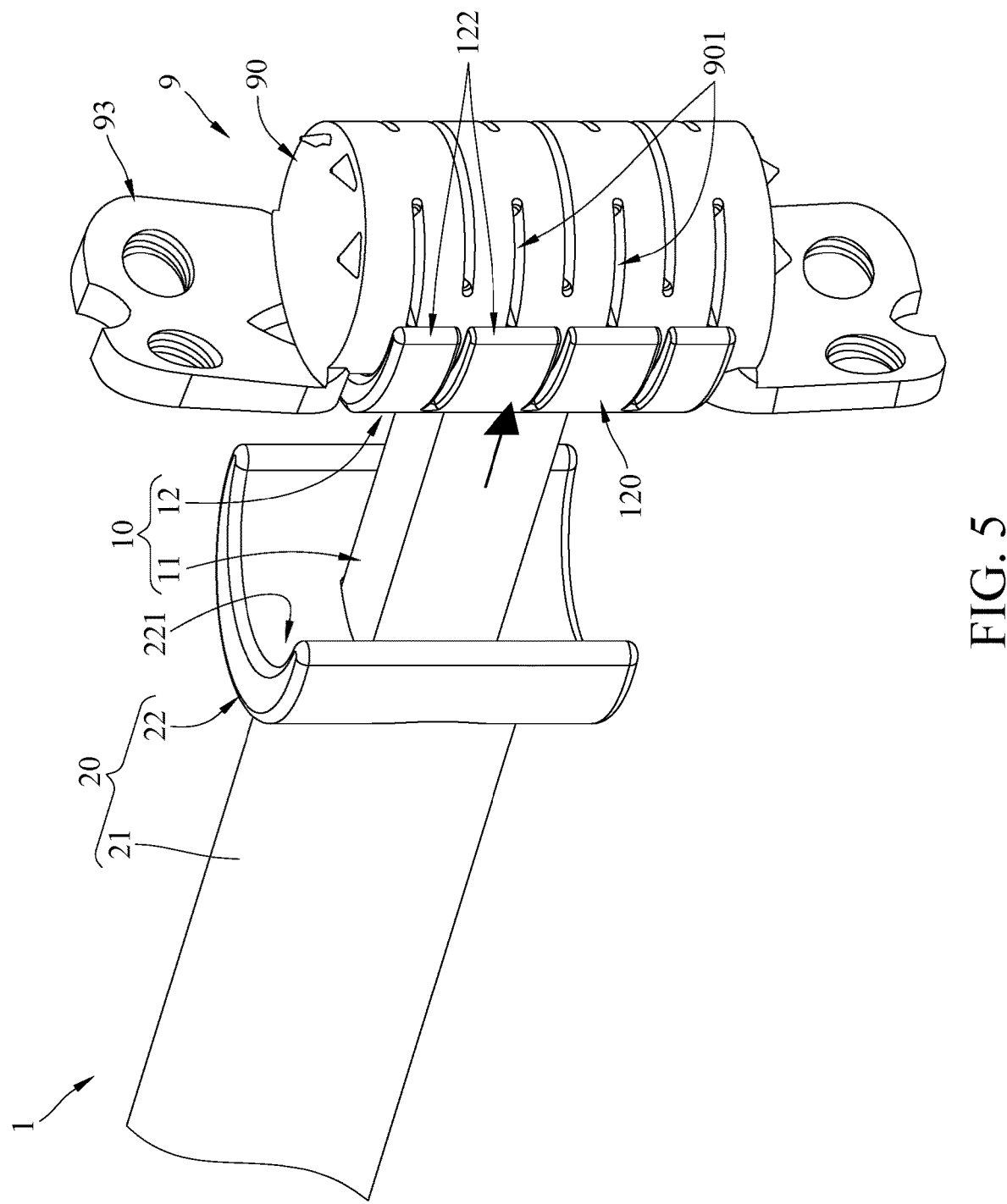
FIG. 5 to FIG. 11 are schematic views showing mounting process of the implant operated by the surgical tool in FIG. 1.

Hereinafter, please further refer to FIG. 2 to FIG. 4 together with FIG. 1 for the detailed illustration of the surgical tool 1. In this embodiment, the surgical tool 1 is suitable for holding the implant 9 and may include an inner rod 10 and a sleeve 20. The inner rod 10 is a component of the surgical tool 1 suitable for pushing the implant 9 so as to force the implant 9 to be mounted into the space between the vertebrae 8. The sleeve 20 is slidably sleeved on the inner rod 10. The sleeve 20 is a component of the surgical tool 1 beneficial to allow the inner rod 10 to firmly push the implant 9.

In this embodiment, the inner rod 10 may include a rod portion 11 and a holding portion 12. The rod portion 11 is a portion of the inner rod 10 which is a general straight stick extending in one direction. Optionally, the rod portion 11 of the inner rod 10 may be a non-round stick; that is, the rod portion 11 of the inner rod 10 has a non-circular cross section. For example, in this embodiment, the rod portion 11 of the inner rod 10 may have a first positioning surface 111 which is a flat surface. Moreover, the first positioning surface 111 may be a flat surface of the rod portion 11 extending from end to end. Note that the rod portion 11 of the inner rod 10 is not limited to the configuration shown in the drawings. In some other embodiments, as long as the rod portion of the inner rod is a non-round stick, the rod portion of the inner rod may have a cross section being triangular, quadrangular, other polygonal, or even irregular.

The holding portion 12 is located at one end of the rod portion 11. For example, the holding portion 12 may be integrally formed at one end of the rod portion 11. However, the present disclosure is not limited thereto. In some other embodiments, the holding portion may be mounted at one end of the rod portion 11 by screwing, engaging, adhering, etc. Further, the holding portion 12 may have a contour matching the flexible body 90 of the implant 9. For example, the holding portion 12 may be C-shaped and can surround a first accommodation space S1. As such, the holding portion 12 can match the substantially columnar flexible body 90 of the implant 9. When the holding portion 12 is attached on the flexible body 90 of the implant 9, the holding portion 12 is able to abut on or press against at least partial contour of the flexible body 90, such that the flexible body 90 is partially accommodated into the first accommodation space S1 of the holding portion 12.

The holding portion 12 may have a pressed surface 120 and a pressing surface 121. The pressed surface 120 is a surface of the holding portion 12 suitable for directly receiving the pressing or the pressure from the sleeve 20. The pressing surface 121 is a surface of the holding portion 12 suitable for directly pressing or pushing the flexible body 90 of the implant 9. Note that the first accommodation space S1 is defined by the surrounding of the pressing surface 121.

Further, in the inner rod 10, the whole or at least the holding portion 12 of the inner rod 10 is made of elastically deformable material. Therefore, when an external force is applied on the holding portion 12, the holding portion 12 is able to be elastically deformed in response to the applied force, and the first accommodation space S1 surrounded by the holding portion 12 is therefore shrunk in response to the applied force. For example, in this embodiment, the holding portion 12 may further include a plurality of elastic arms 122. As shown in FIG. 2, the elastic arms 122 are spaced apart from one another and are disposed at two opposite sides of the holding portion 12. The elastic arms 122 are parts of the holding portion 12 suitable for being elastically deformed due to the influence of the external force.

Moreover, the inner rod 10 may further include one or more fin portions 123 protruded from the holding portion 12. For example, the fin portions 123 may be protruded from the pressing surface 121 of the holding portion 12 and thus located in the first accommodation space S1. Specifically, the fin portions 123 are respectively protruded from the elastic arms 122 on the pressing surface 121 and thus located in the first accommodation space S1. As such, when the elastic arms 122 are elastically deformed due to the external force, the elastic arms 122 are able to move the fin portions 123. Note that the quantity, thickness, length, shape and the distribution of the fin portions 123 can correspond to the slots 901 of the implant 9 to be inserted. However, the present disclosure is not limited thereto. In some other embodiments, the quantity of the fin portions protruded from the holding portion of the inner rod may be only one or more than the quantity of the slots of the implant to be inserted. With the configuration of the fin portions 123 corresponding to the slots 901 of the implant 9 according to the present disclosure, each fin portion 123 would be forced and moved to be engaged in the respect slot when the elastic arms 122 are elastically deformed due to the external force, such that the implant 9 is able to be firmly embedded and immobilized to the holding portion 12.

In this embodiment, the sleeve 20 may include a sleeving portion 21 and a retaining portion 22. The sleeving portion 21 is a portion of the sleeve 20 which is a general straight stick extending in one direction. The sleeving portion 21 is slidably sleeved on the rod portion 11 of the inner rod 10. The retaining portion 22 is located at one end of the sleeving portion 21. For example, the retaining portion 22 may be located at one end of the sleeving portion 21 close to the holding portion 12 of the inner rod 10. The retaining portion 22 may be integrally formed at one end of the sleeving portion 21. However, the present disclosure is not limited thereto. In some other embodiments, the retaining portion 22 may be mounted at one end of the sleeving portion by screwing, engaging, adhering, etc.

The retaining portion 22 may have a contour matching the holding portion 12 of the inner rod 10 and thus is able to selectively and directly press against the holding portion 12 of the inner rod 10. For example, the retaining portion 22 may have a contour matching the pressed surface 120 of the holding portion 12 of the inner rod 10 and can surround a second accommodation space S2. As such, the retaining portion 22 can match the C-shaped holding portion 12 of the inner rod 10. When the retaining portion 22 is attached on the pressed surface 120 of the holding portion 12 of the inner rod 10, the retaining portion 22 is able to abut on or press against at least partial contour of the pressed surface 120 of the holding portion 12, such that the holding portion 12 is partially accommodated into the second accommodation space S2.

The retaining portion 22 may have a retaining surface 221. The retaining surface 221 is a surface of the retaining portion 22 suitable for selectively and directly pressing or pushing the pressed surface 120 of the holding portion 12 of the inner rod 10. Note that the second accommodation space S2 is defined by the surrounding of the retaining surface 221. Note that in some cases where the flexible body 90 of the implant 9 is substantially columnar, the retaining surface 221 of the retaining portion 22 of the sleeve 20 may have a curvature radius less than the curvature radius of the pressed surface 120 of the holding portion 12 of the inner rod 10. The retaining portion 22 of the sleeve 20 may further has two opposite distal ends 222. The elastic arms 122 are located on the movement path P of the distal ends 222 of the retaining portion 22 of the sleeve 20 so as to ensure the distal ends 222 are able to push the elastic arms 122 of the holding portion 12 during the movement of the retaining portion 22 of the sleeve 20 towards the holding portion 12 of the inner rod, thereby achieving the effect of the shrinkage of the first accommodation space S1 due to the elastic deformation of the holding portion 12 affected by the sleeve 20.

The sleeve 20 may be hollow. Specifically, the sleeve 20 may further include an inner tubular wall 231. The inner tubular wall 231 can surround a through hole 23, and the through hole 23 is defined by the surrounding of the inner tubular wall 231. The through hole is disposed through the sleeving portion 21 and the retaining portion 22 and has a shape matching the rod portion 11 of the inner rod 10. As such, the rod portion 11 of the inner rod is able to be disposed through the through hole 23 so as to be disposed in the sleeving portion 21 and the retaining portion 22 of the sleeve 20. By doing so, the sleeving portion 21 is slidably sleeved on the rod portion 11 of the inner rod 10, and the retaining portion 22 is able to move close to or away from the holding portion 12 of the inner rod 10.

Optionally, the through hole 23 of the sleeve 20 may be non-cylindrical; that is, the through hole 23 of the sleeve 20 has a non-circular cross section. For example, in this embodiment, the inner tubular wall 231 defining the through hole 23 may have a second positioning surface 2311 which is a flat surface. Moreover, the second positioning surface 2311 may be a flat surface of the inner tubular wall 231 extending from end to end of the through hole 23. When the rod portion 11 of the inner rod 10 is disposed through the through hole 23 of the sleeve 20, the second positioning surface 2311 of the through hole 23 of the sleeve 20 can correspond to or touch the first positioning surface 111 of the rod portion 11 of the inner rod 10. By doing so, the sleeve 20 is restricted to the linear sliding in the extension direction of the rod portion 11 of the inner rod 10 and cannot be rotated about the rod portion 11 due to the plane-to-plane relative positional relationship between the rod portion 11 of the inner rod 10 and the though hole 23 of the sleeve 20 (i.e., the correspondence between the first positioning surface 111 and the second positioning surface 2311); that is, when the sleeve 20 is sleeved on the inner rod 10, the inner rod 10 and the sleeve 20 can only slide with respect to each other in the axial direction instead of relative rotation. This is favorable for improving the stability and convenience of the subsequence operation. Similarly, note that the through hole of the sleeve is not limited to the configuration shown in the drawings. In some other embodiments, as long as the through hole of the sleeve is able to match the contour of the rod portion of the inner rod, the through hole of the sleeve may have a cross section being triangular, quadrangular, other polygonal, or even irregular.

Optionally, the surgical tool 1 may further include a handle 30 connected to the other end of the rod portion 11 of the inner rod 10. Specifically, the handle 30 and the holding portion 12 of the inner rod 10 are respectively located at two opposite ends of the rod portion 11 of the inner rod 10. The handle 30 is a component of the surgical tool 1 suitable for being held by users and for receiving the tapping during the usage of the surgical tool 1 or bearing the impact or pressure during the mounting of the implant 9. The sleeve 20 is movably located between the handle 30 and the holding portion 12 of the inner rod 10.

Optionally, the surgical tool 1 may further include a positioner 40. For correspondence, the sleeving portion 21 of the sleeve 20 may have a screw hole 211. The screw hole 211 may be disposed through the sleeving portion 21 of the sleeve 20 to be connected to the through hole 23 of the sleeve 20. As such, when the positioner 40 is disposed through the screw hole 211 of the sleeve 20, the positioner 40 is able to selectively press against the rod portion 11 of the inner rod 10 located in the through hole 23 of the sleeve 20, so that the sliding resistance of the sleeving portion 21 of the sleeve 20 with respect to the rod portion 11 of the inner rod 10 can be increased, thereby securing or fixing the relative positional relationship between the sleeving portion 21 of the sleeve 20 and the rod portion 11 of the inner rod 10. That is, when the positioner 40 is disposed through the sleeving portion 21 and presses against the rod portion 11 of the sleeving portion 21, the sleeving portion 21 can be firmly sleeved on the rod portion 11 and not easily slides with respect to the rod portion 11.

Then, please further refer to FIG. 5 to FIG. 11 for illustrating how to mount the implant 9 by the surgical tool 1. First, please refer to FIG. 1, FIG. 5 and FIG. 6, the holding portion 12 of the inner rod 10 can abut on the flexible body 90 of the implant 9 along a direction denoted by the arrow of FIG. 5 and FIG. 6, and the fin portions 123 protruded from the elastic arms 122 of the holding portion 12 can be respectively inserted into the slots 901 of the flexible body 90. At this time, the surgical tool 1 can hold the implant 9 while maintaining the current shape of the flexible body 90 of the implant 9 through the contour matching between the holding portion 12 and the flexible body 90 of the implant 9 as well as the insertion manner of the fin portions 123 into the slots 901 of the flexible body 90.

Figure 6:
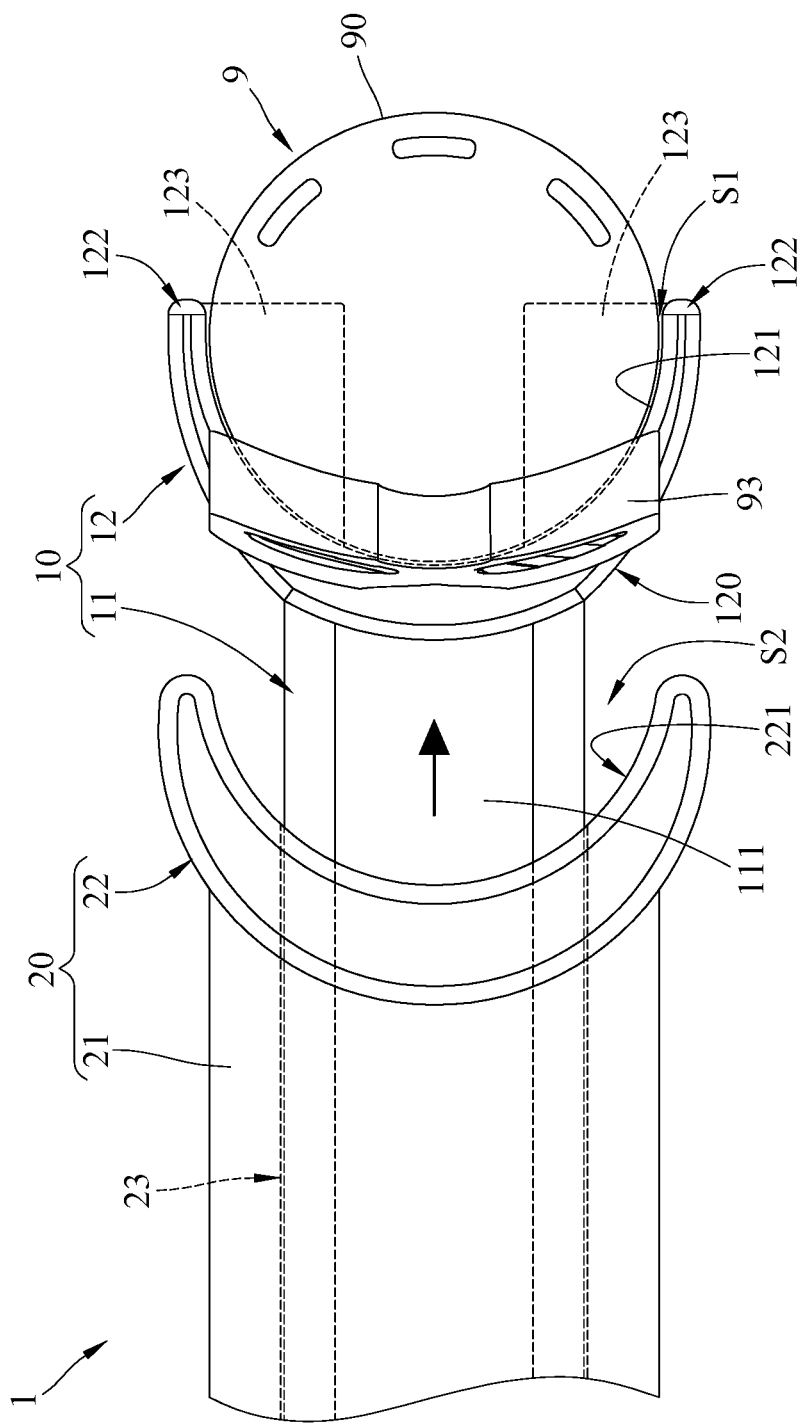
Figure 7:
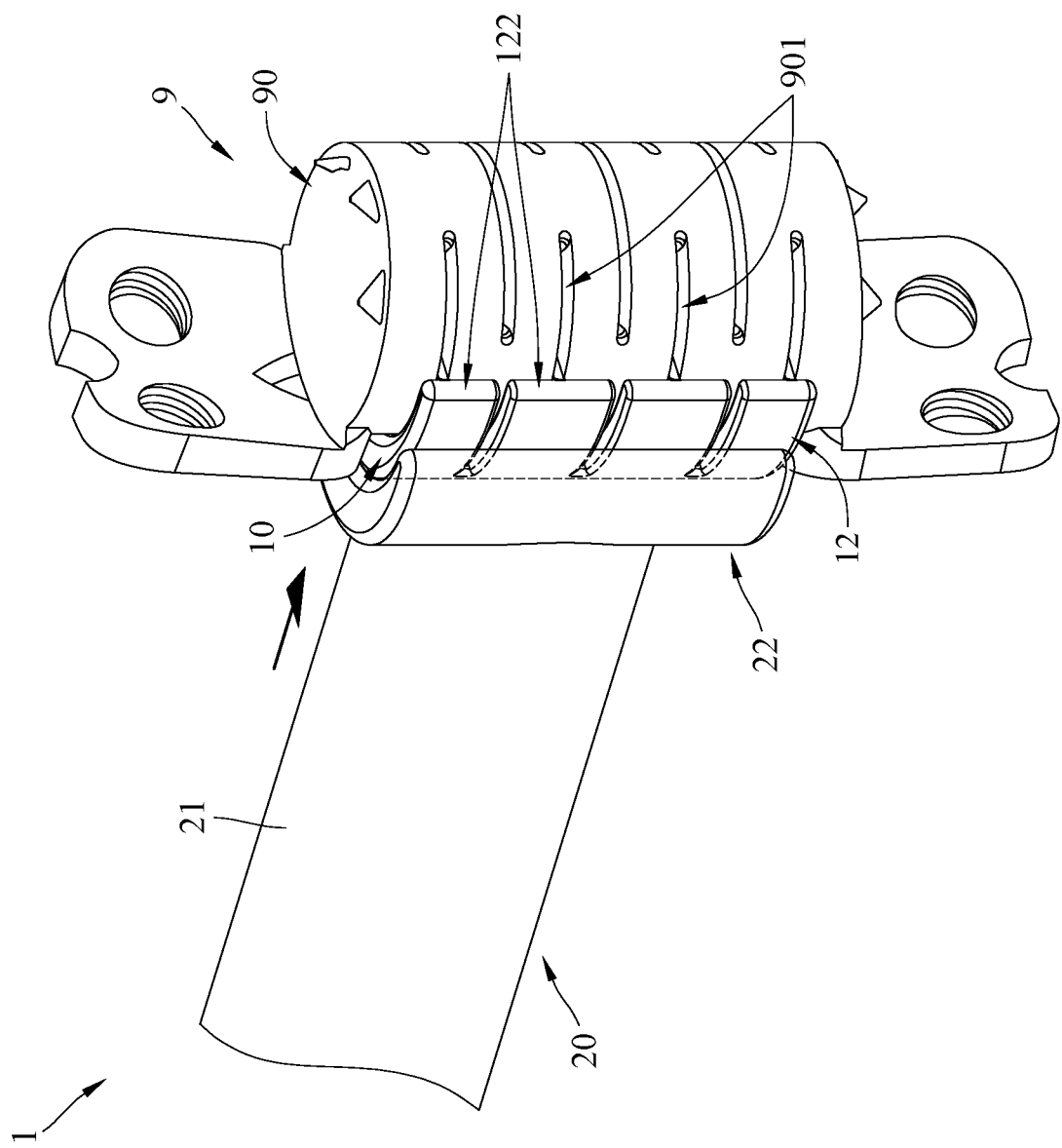

Then, please refer to FIG. 6 to FIG. 7, the sleeve 20 can be slid towards the holding portion 12 of the inner rod 10, such that the retaining portion 22 of the sleeve 20 presses against the elastic arms 122 of the holding portion 12 of the inner rod 10. As discussed, since the curvature radius of the retaining surface 221 of the retaining portion 22 of the sleeve 20 is less than the curvature radius of the pressed surface 120 of the holding portion 12 of the inner rod 10, the elastic arms 122 of the inner rod 10 can be elastically deformed due to the pressure from the retaining portion 22 of the sleeve 20, thereby shrinking the first accommodation space S1 of the holding portion 12 and allowing the fin portions 123 on the elastic arms 122 to move deeper towards the inner side of the flexible body 90 of the implant 9. Accordingly, the surgical tool 1 can further strengthen the holding force on the implant 9 and maintaining the holding stability on the flexible body 90 of the implant 9 through the pressing manner of the retaining portion 22 on the holding portion 12.

In one embodiment of the present disclosure, the holding area of the holding portion 12 can be further designed for ensuring a sufficient holding force of the surgical tool 1 on the implant 9. In detail, since the holding portion 12 holds the implant 9 through the elastic arms 122 and the pressing surface 121, the holding force of the surgical tool 1 on the implant 9 is affected by the covering of the elastic arms 122 and the pressing surface 121 on the implant 9. In one embodiment of the present disclosure, the elastic arms 122 and the pressing surface 121 of the holding portion 12 can be designed to have a holding area which covers the implant 9 with an arc of approximate 60 degrees to approximate 180 degrees (i.e., the contact area of the elastic arms 122 and the pressing surface 121 on the implant 9) with respect to the cross section of the implant 9, but the present disclosure is not limited thereto.

Figure 8:
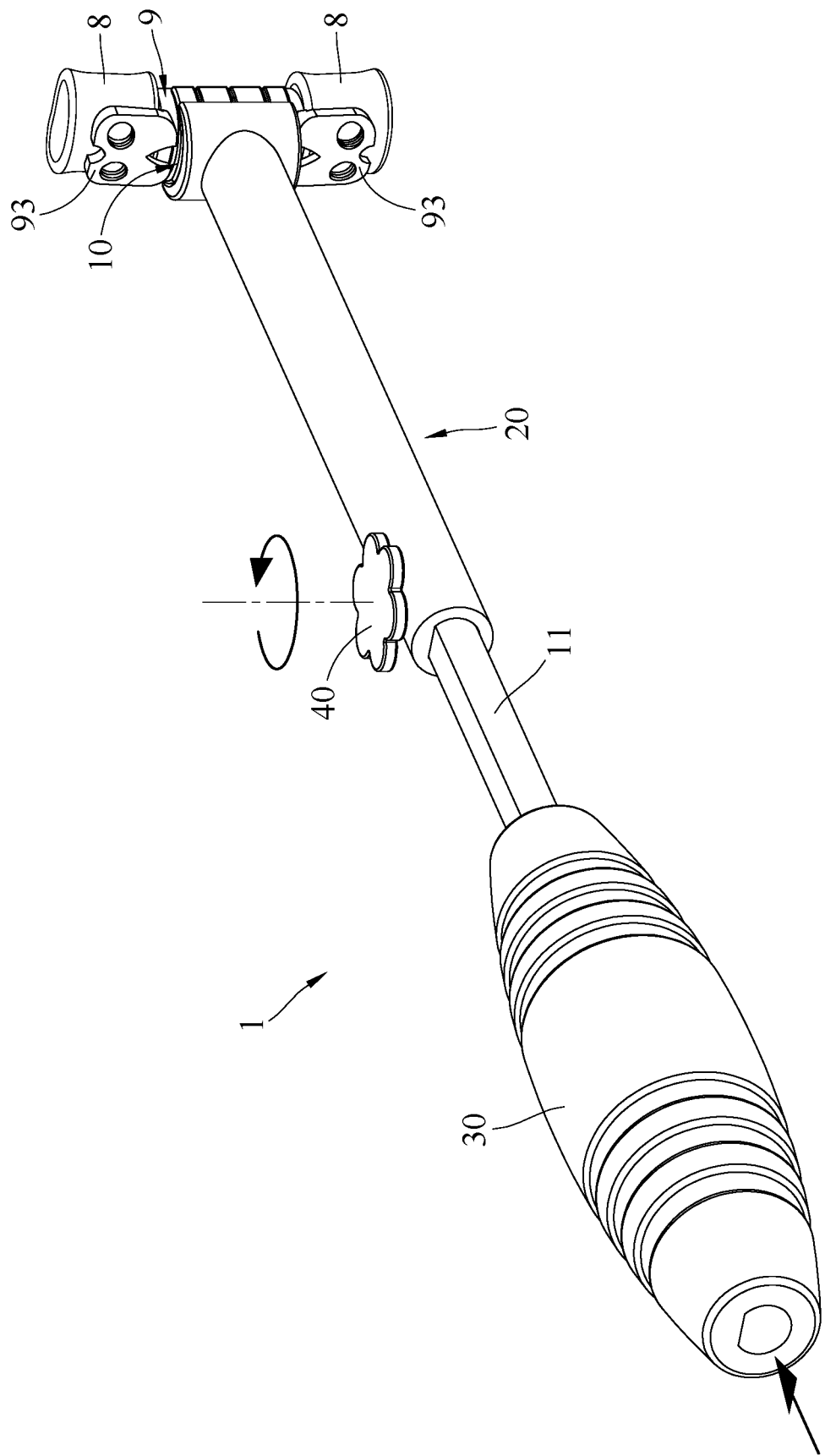
Figure 9:
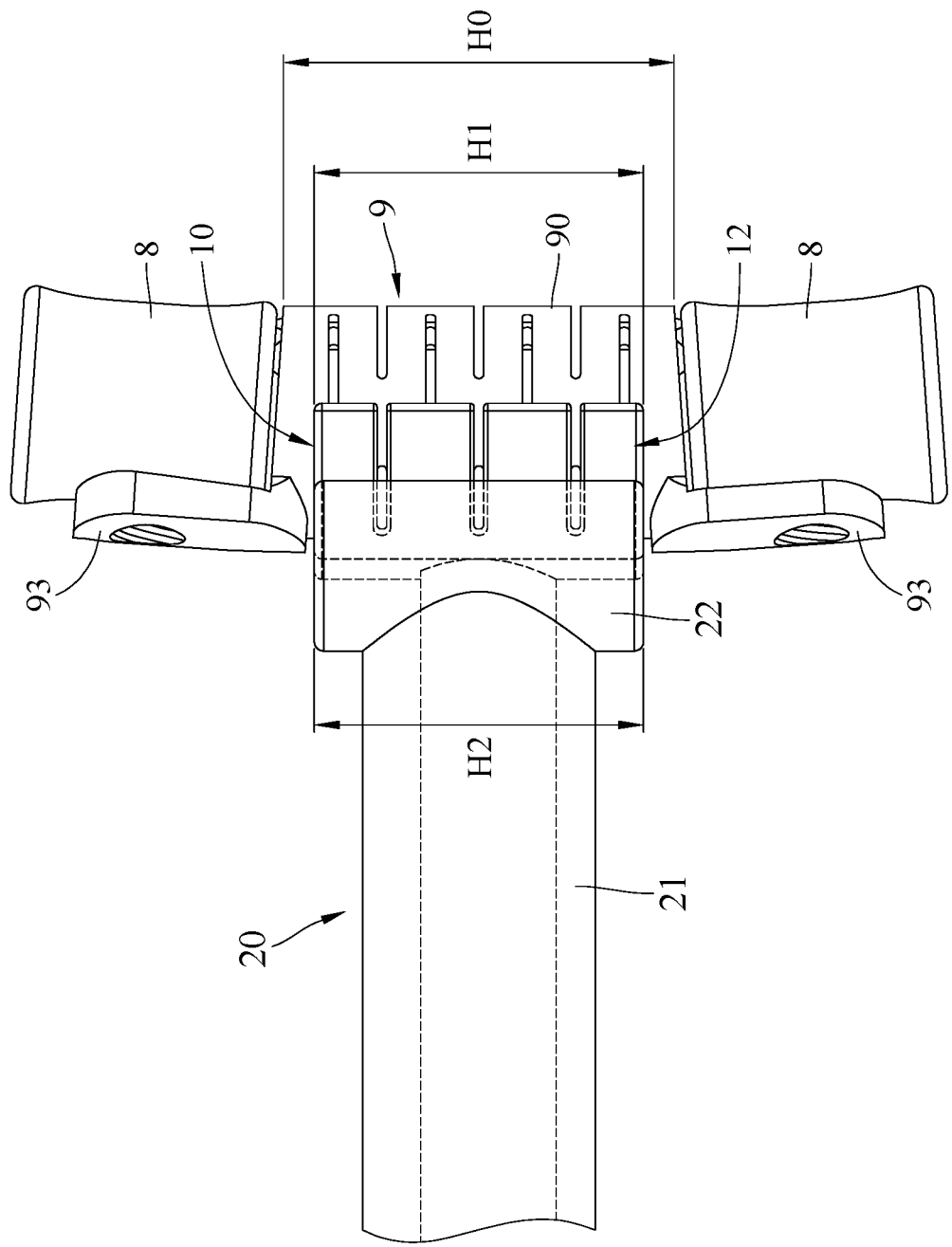

Then, as shown in FIG. 8 to FIG. 9, the positioner 40 can be rotated to be disposed through the sleeve 20 and thus to press against the rod portion 11 of the inner rod 10, thereby preventing any relative sliding between the sleeve 20 and the inner rod 10 in the subsequence process. Then, the surgical tool 1 can be used to place the implant 9 into the space between the vertebrae 8, and the handle 30 can be tapped by any suitable tool. Due to the connection between the handle 30 and the rod portion 11 of the inner rod 10, the tapping or pressing force on the handle 30 can be transmitted to the implant 9 via the handle 30 and the inner rod thereby moving the implant 9 into the space between the vertebrae 8.

In addition, the sizes of the holding portion 12 of the inner rod 10 and the retaining portion 22 of the sleeve 20 can be designed in consideration of the size of the flexible body of the implant 9, such that the inner rod 10 can evenly push the implant 9 without unwanted deformation of the flexible body 90 of the implant 9, and the sleeve 20 can make the holding portion 12 of the inner rod 10 to firmly hold the flexible body 90 of the implant 9 during the movement of the implant 9 caused by the tapping on the surgical tool 1. As shown in FIG. 9, the height of the flexible body 90 of the implant 9 is defined as H0, the height of the holding portion 12 of the inner rod 10 is defined as H1, the height of the retaining portion 22 of the sleeve 20 is defined as H2, and the following conditions may be satisfied: $(3/4) \times H0 \leq H1 \leq H0$; and $H2 \leq H1$.

Figure 10:
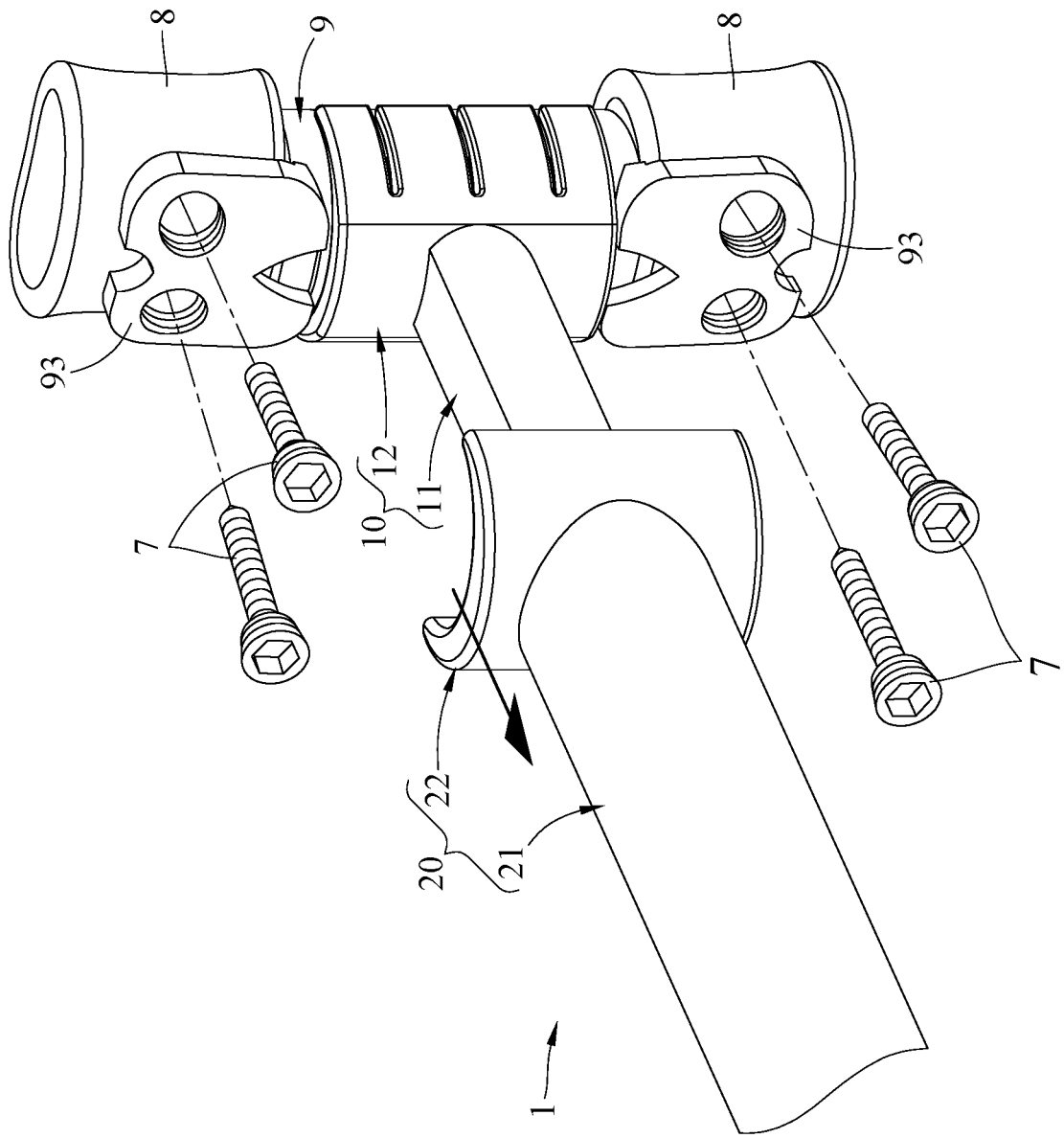
Figure 11:
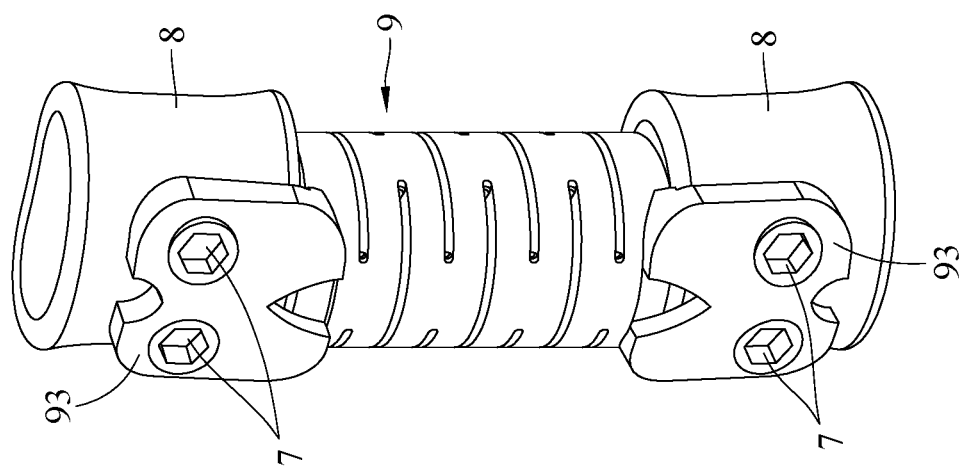

Then, as shown in FIG. 10 to FIG. 11, the screws 7 can be screwed to the vertebrae 8 via the tabs 93 of the implant 9, so that the implant 9 can be firmly secured between the vertebrae 8. The screws 7 described herein may be, but not limited to, pedicle screws which are commonly used in vertebral reconstruction implants. When the implant 9 is firmly immobilized, the positioner 40 can be rotated to release the pressing of the positioner 40 against the rod portion 11 of the inner rod 10. Then, the sleeve 20 is moved along a direction denoted by the arrow so as to release the pressing and the pressure of the retaining portion 22 of the sleeve 20 against the holding portion 12 of the inner rod 10. Finally, as shown in FIG. 11, the surgical tool 1 is removed away from the flexible body 90 of the implant 9 to finish the mounting process of the implant 9 between the vertebrae 8.

Figure 12:
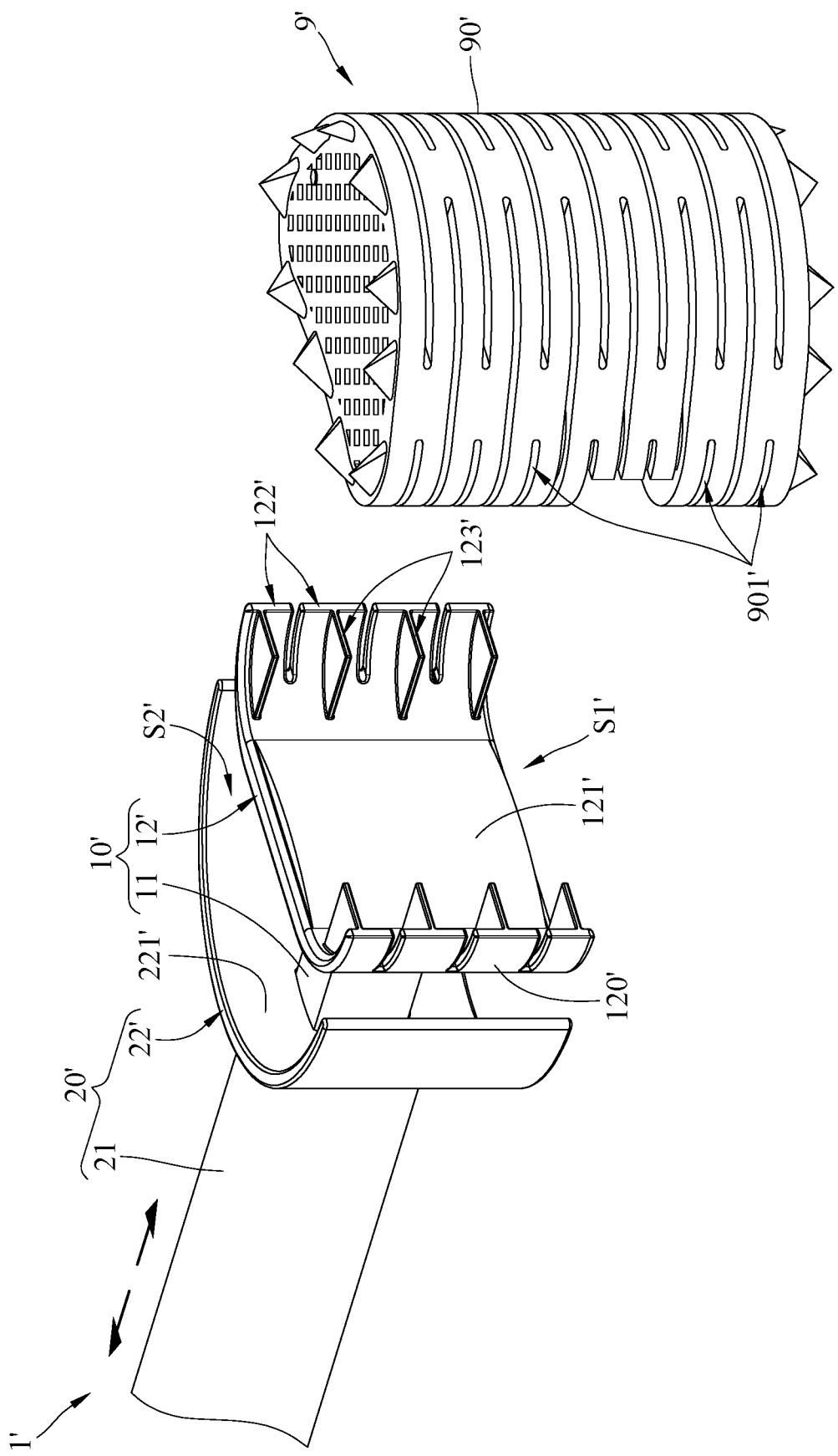
FIG. 12 is a schematic view showing a surgical tool according to another embodiment of the present disclosure being suitable for an implant.

Note that the surgical tool 1 discussed above is only exemplary in one embodiment of the present disclosure and is not intended to limit the present disclosure. It should be understood that the configuration of the implant can be correspondingly adjusted or modified based on the parts to be implanted. Certainly, the surgical tool of the present disclosure can be accordingly adjusted or modified to be suitable for the mounting of the implant. For example, please refer to FIG. 12, another embodiment of the present disclosure provides a surgical tool 1' suitable for another space between vertebrae. As shown in FIG. 12, the surgical tool 1' is suitable for holding an implant 9'. According to the contour of the implant 9', it can be known that the implant 9' is a vertebral reconstruction implant suitable for lumbar vertebrae. In this case, the pressing surface 121' of the holding portion 12' of inner rod 10' of the surgical tool 1', the first accommodation space S1' surrounded and defined by the pressing surface 121', and the elastic arms 122' of the holding portion 12' may each have a contour corresponding to one side of the flexible body 90' of the implant 9', and the fin portions 123' on the elastic arms 122' may have a distribution and size corresponding to the slots 901' of the flexible body 90'. Correspondingly, the sleeve 20' of the holding portion 12' suitable for retaining and deforming, the retaining surface 221' of the retaining portion 22' of the sleeve 20', and the second accommodation space S2' surrounded and defined by the retaining surface 221' may each have a contour corresponding to the pressed surface 120' of the holding portion 12'. Similarly, the surgical tool 1' can mount the implant 9' by adopting the mounting process discussed above and depicted in FIG. 5 to FIG. 10, which is not repeated herein.

Note that that as long as the surgical tool is suitable for the contour and design of the implant to be mounted, shapes or the sizes such as thickness, length, width and height of the surgical tool and any portion thereof according to the present disclosure can be modified or adjusted based on any actual requirement, and the present disclosure is not limited thereto.

According to the surgical tool for implant discussed above, since the fin portions on the holding portion of the inner rod can be respectively inserted into the slots of the implant, the surgical tool can hold the implant while maintaining the current shape of the implant through the accommodation for the implant into the first accommodation space of the holding portion and the insertion manner of the fin portions into the slots. Also, the sleeve slidable on the rod portion of the inner rod can force the retaining portion to elastically deform the holding portion of the inner rod. Therefore, the surgical tool can further strengthen the holding force on the implant and allow the fin portions on the holding portion to move deeper towards the slots of the implant through the pressing manner of the retaining portion on the holding portion, thereby improving the shape stability of the implant. Accordingly, the surgical tool of the present disclosure is able to prevent unwanted movement or unwanted deformation of the implant during the mounting process, thereby significantly reducing the difficulty of the implant mounting and advantageously reducing the probability of fusion failure caused by improper implant mounting.

The embodiments are chosen and described in order to best explain the principles of the present disclosure and its practical applications, to thereby enable others skilled in the art best utilize the present disclosure and various embodiments with various modifications as are suited to the particular use being contemplated. It is intended that the scope of the present disclosure is defined by the following claims and their equivalents.

What is claimed is:

1. A surgical tool, configured for holding an implant, comprising:
    an inner rod, comprising a rod portion and a holding portion, wherein the holding portion is located at one end of the rod portion and has a first accommodation space which is configured for accommodating at least part of the implant; and
    a sleeve, comprising a sleeving portion and a retaining portion, wherein the sleeving portion is slidably sleeved on the rod portion of the inner rod, and the retaining portion is located at one end of the sleeving portion and selectively presses against the holding portion;
    wherein the inner rod further comprises at least one fin portion protruded from the holding portion and located in the first accommodation space, and the at least one fin portion is configured to be inserted into at least one slot of the implant.

2. The surgical tool according to claim 1, wherein the holding portion of the inner rod comprises a plurality of elastic arms which are spaced apart from one another and are disposed at two opposite sides of the holding portion.

3. The surgical tool according to claim 2, wherein the at least one fin portion is protruded from one of the plurality of elastic arms.

4. The surgical tool according to claim 2, wherein the plurality of elastic arms are located on a movement path of two opposite distal ends of the retaining portion of the sleeve.

5. The surgical tool according to claim 1, further comprising a handle connected to another end of the rod portion of the inner rod, wherein the sleeve is movably located between the handle and the holding portion of the inner rod.

6. The surgical tool according to claim 1, further comprising a positioner, wherein the sleeving portion of the sleeve has a screw hole disposed through the sleeving portion;

when the positioner is disposed through the screw hole, and the positioner selectively press against the rod portion of the inner rod located in the sleeve.

7. The surgical tool according to claim 1, wherein the sleeve further comprises an inner tubular wall surround a through hole, the through hole is disposed through the sleeving portion and the retaining portion, and the rod portion of the inner rod is disposed through the through hole.

8. The surgical tool according to claim 7, wherein the rod portion of the inner rod has a first positioning surface which is a flat surface and extends from the end of the rod portion to another end of the rod portion, the inner tubular wall has a second positioning surface which is a flat surface and extends from one end of the through hole to another end of the through hole, and the second positioning surface corresponds to the first positioning surface.

9. The surgical tool according to claim 1, wherein the retaining portion of the sleeve has a retaining surface, the holding portion of the inner rod has a pressed surface, the retaining surface is selectively and directly press against the pressed surface, and a curvature radius of the retaining surface is less than a curvature radius of the pressed surface.

10. The surgical tool according to claim 1, wherein the implant has a height H0, the holding portion of the inner rod has a height H1, the retaining portion of the sleeve has a height H2, and following conditions are satisfied: $(3/4) \times H0 \leq H1 \leq H0$; and $H2 \leq H1$.

11. The surgical tool according to claim 1, wherein a holding area of the holding portion which configured to cover the implant has an arc ranging from 60 degrees to 180 degrees with respect to a cross section of the implant.

* * * * *